United States Patent [19]

Tsuda et al.

[11] Patent Number: 5,744,659
[45] Date of Patent: Apr. 28, 1998

[54] PROCESS FOR THE PREPARATION OF DIFLUOROMETHANE

[75] Inventors: Takehide Tsuda; Yasufu Yamada; Takashi Shibanuma, all of Osaka, Japan

[73] Assignee: Daikin Industries, Ltd., Osaka, Japan

[21] Appl. No.: 750,836

[22] PCT Filed: Jun. 7, 1995

[86] PCT No.: PCT/JP95/01122

§ 371 Date: Dec. 19, 1996

§ 102(e) Date: Dec. 19, 1996

[87] PCT Pub. No.: WO95/35271

PCT Pub. Date: Dec. 28, 1995

[30] Foreign Application Priority Data

Jun. 20, 1994 [JP] Japan .................................. 6-137275

[51] Int. Cl.$^6$ .............................. C07C 17/20; C07C 19/08
[52] U.S. Cl. ................................ 570/167; 570/165
[58] Field of Search ................................ 570/167, 165

[56] References Cited

U.S. PATENT DOCUMENTS

| 2,005,711 | 6/1935 | Daudt et al. | |
|---|---|---|---|
| 2,749,374 | 6/1956 | Ruh et al. | 570/170 |
| 2,749,375 | 6/1956 | Ruh et al. | 570/170 |
| 4,138,355 | 2/1979 | Ferstandig | 252/182 |
| 5,208,395 | 5/1993 | Elsheikh | 570/166 |
| 5,495,057 | 2/1996 | Nam et al. | 570/167 |

*Primary Examiner*—Alan L. Rotman
*Assistant Examiner*—Lyman H. Smith
*Attorney, Agent, or Firm*—Birch, Stewart, Kolasch & Birch, LLP

[57] ABSTRACT

Difluoromethane is prepared by reacting dichloromethane and hydrogen fluoride in a liquid phase in the presence of a fluorination catalyst under reaction conditions in which the reaction pressure is between 1 and 10 kg/cm$^2$ab., and the reaction temperature is between 50 and 150° C., provided that the selected reaction temperature is higher than a temperature at which hydrogen fluoride is not liquefied under the selected reaction pressure.

Under the above conditions, the conversions of dichloromethane and HF are very high, and amounts of by-products other than R30 are very low, typically less than 0.1% per difluoromethane, when the unreacted materials are recycled.

A material of a reactor is hardly corroded by the reaction using an antimony chlorofluoride and HF which are highly corrosive, as long as the above conditions are maintained.

9 Claims, No Drawings

PROCESS FOR THE PREPARATION OF DIFLUOROMETHANE

FIELD OF THE INVENTION

This application is a 35 USC 371 National Stage Filing of PCT/JP95/01122, published as WO/95/35271 on Dec. 28, 1995.

The present invention relates to a process for the preparation of difluoromethane comprising fluorinating dichloromethane with hydrogen fluoride in a liquid phase in the presence of a catalyst.

PRIOR ART

Difluoromethane (hereinafter referred to as "R32") attracts attention as a substitute refrigerant for chlorodifluoromethane which is used as a refrigerant for air conditioners.

It is known that R32 is prepared by reacting dichloromethane (hereinafter referred to as "R30") with hydrogen fluoride (HF) in a gas or liquid phase in the presence of a catalyst.

U.S. Pat. Nos. 2,749,374 and 2,749,375 disclose a process for the preparation of R32 comprising reacting R30 and HF in a liquid phase at a temperature between 110 and 175° C. in the presence of an antimony chlorofluoride catalyst ($SbCl_xF_y$ in which x +y=3,y/(x+y)=0.8 and Sb(V)>5%). However, this process produces a large amount of by-products of R40 series such as monochlorometane (hereinafter referred to as "R40") and fluoromethane (hereinafter referred to as "R41") which are undesirable impurities in addition to R30 and decrease the yield of R32. It is very important for the reaction system not to corrode the materials of reaction apparatuses in the production of R32, but HF and halogenated antimony are known to corrode such the materials. Neither of the above U.S. Pat. Nos. describe that the materials of reaction apparatuses had the corrosion resistance when the reaction was performed under the above conditions.

U.S. Pat. No. 4,138,355 discloses the addition of an equimolar amount of antimony trihalide to antimony pentahalide to prevent the corrosion of a reactor caused by a mixture of halogen-containing organic compounds with HF and antimony pentahalide. However, the composition of the catalyst may vary with the progress of the reaction since the amount of antimony trihalide increases due to the degradation of the catalyst.

JP-A-59-231030 discloses a process for the preparation of R32 comprising reacting R30 and HF in a gas phase at a temperature of 200° C. in the presence of aluminum fluoride or chromium fluoride as a catalyst. This process is not economically advantageous since the reaction temperature is as high as 200° C. and the gas phase reaction requires more complicated apparatuses than the liquid phase reaction.

SUMMARY OF THE INVENTION

An object of the present invention is to solve the above problems associated with the prior art and to provide a process for preparing R32 economically and safely.

Accordingly, the present invention provides a process for the preparation of R32 comprising reacting R30 and HF in a liquid phase in the presence of a fluorination catalyst, wherein the reaction pressure is between 1 and 10 kg/cm²ab., and the reaction temperature is between 50° and 150° C., provided that the selected reaction temperature is higher than a temperature at which HF is not liquefied under the selected reaction pressure.

DETAILED DESCRIPTION OF THE INVENTION

Examples of the fluorination catalyst used in the process of present invention are antimony chlorofluorides, titanium chlorofluorides, tin chlorofluorides, and the like. A preferable catalyst is an antimony chlorofluoride of the general formula:

$$SbCl_xF_y$$

wherein x+y=5. In particular, the antimony chlorofluoride of the above formula in which y is a number of between 1 and 4 is preferable. When y is less than 1 (one), the conversion of R30 is low and the yield of R32 per unit weight of the catalyst decreases. Therefore, a large amount of the catalyst should be used. Nevertheless, the antimony catalyst of the general formula in which the index y is between 0.5 and 1 may be used. When the index y is larger than 4, the process is less economical since a large amount of HF should be recycled. The index y is preferably between 2 and 3.

The antimony chlorofluoride is a chlorofluoride of pentavalent antimony prepared in situ by partial fluorination of antimony pentachloride. As described above, the index y in the antimony chlorofluoride of the above formula is preferably between 1 and 4. The ratio of x to y may vary and therefore the catalyst may lose its activity as the reaction proceeds in the conventional processes. However, the index y can be maintained in the above range under the reaction conditions according to the present invention.

The fluorination catalyst is used in an amount of between 10 and 90 mole % in the liquid reaction mixture. When the amount of the catalyst is less than 10 mole %, the residence time of the reaction gas is prolonged, the amount of the R40 series impurities increases, and therefore the product must be purified in some cases. When the amount of the catalyst exceeds 90 mole %, the amount of the organic materials is too small, the amount of the catalyst entrained in the splashed liquid increases, and therefore pipes and other equipments tend to be clogged. The more preferable amount is between 40 and 70 mole %, while it may depend on the reaction temperature.

The reaction pressure is between 1 and 10 kg/cm²ab., preferably between 5 and 10 kg/cm²ab.

The reaction temperature should be in the range between 50° and 150° C., provided that the selected reaction temperature is a temperature at which HF is not liquefied under the selected reaction pressure. Preferably, the reaction temperature is at least 5° C. higher than the boiling point of HF under the selected reaction pressure. The reason why the present invention sets this limitation is that the corrosion resistance of the reaction apparatuses severely deteriorates and therefore the process cannot be safely performed if liquid state HF is present in the liquid reaction mixture. R30 is present mainly in the liquid phase, while HF is present mainly in the gas phase in the process of the present invention.

The process of the present invention in a preferred embodiment can be performed by the following steps:

(1) First, the fluorination catalyst is charged into a reactor.

(2) Then, R30 and HF are charged into the reactor to effect the reaction. The reaction is performed under the above described reaction conditions, and thus R32 and chlorofluoromethane (hereinafter referred to as "R31") which is an intermediate are produced.

This reaction can be performed in a generally known apparatus. In general, the reactor is required to be supplied with the raw materials (R30 and HF) and recycled materials (R31, R30 and HF) which will be explained below, in the liquid or gas state and to heat or cool the liquid reaction mixture sufficiently. Furthermore, the reactor is required to facilitate the contact between the reactants by a suitable mixing method. In addition, the reactor should maintain the reaction temperature in the range in which HF in the liquid reaction mixture is not liquefied under the selected pressure, even when HF is charged in the liquid state into the reactor.

(3) A portion or whole of the reaction mixture is recovered from the reactor. To this end, a reflux column and a reflux condenser are attached to the reactor, and the reaction mixture is recovered in the form of a refluxed condensed liquid or uncondensed gas. The provision of the reflux column and reflux condenser will prevent the splash of the catalyst together with the reaction mixture.

(4) The recovered reaction mixture is separated to obtain a mixture containing mainly R32 as the reaction product and hydrogen chloride and another mixture containing unreacted R30, HF and intermediate R31. This separation can be effected by distillation since R32 and hydrogen chloride have relatively low boiling points while R30, HF and R31 have relatively high boiling points.

(5) R32 is isolated from the mixture containing R32 and hydrogen chloride by a conventional method such as distillation or washing with water.

(6) The mixture containing unreacted R30, HF and R31 is reused by recycling it to the reactor.

The above process is preferably performed continuously, while it may be performed by a batch process.

Preferable materials used for constructing the reactor which is used in the process of the present invention are Hastelloy C-22, NAR-25-50MTi, double phase stainless steel, SUS, carbon steel and the like. Among them, Hastelloy C-22 and NAR-25-50MTi are particularly preferable.

The present invention will be illustrated by following Examples and Comparative Examples.

EXAMPLE 1

R30 was continuously fluorinated at 100°C. under 6 kg/cm²G in a 600 ml reactor made of Hastelloy C-22 to which a reflux column and a reflux condenser had been attached.

That is, R30 and HF were continuously supplied into the reactor while the reaction product was continuously recovered through the reflux condenser. $SbCl_2F_3$ was used as the catalyst, and the concentration of the catalyst in the reaction liquid was kept constant so that this catalyst composition was maintained.

Sample pieces of various metals for corrosion test, which had been defatted with acetone and weights and sizes of which had been measured, were dipped in the reaction liquid during the continuous fluorination. The corrosion rate was calculated from the weight of each sample piece measured after 8 hours and the surface loss calculation. The results are shown in Table 1.

TABLE 1

| Metal | Corrosion rate (mm/year) |
| --- | --- |
| Carbon steel | 0.75 |
| SUS 316 | 0.25 |
| Double phase stainless steel (DP-3) | 0.07 |
| NAR-25-50MTi | <0.01 |
| Hastelloy C-22 | <0.01 |

It is understood from Table 1 that the metal materials which are used for the construction of the reactor are not excessively corroded under the reaction conditions in the process of the present invention.

EXAMPLE 2

The fluorination was carried out in the same manner as in Example 1 except that the reaction pressure was changed. In this example, the pressure of 15 kg/cm²G was the pressure condition under which HF was liquefied in the reaction mixture at the reaction temperature of 100° C., while 4 kg/cm²G was the pressure condition under which HF was not liquefied. The results are shown in Table 2.

TABLE 2

| Metal | 4 kg/cm² G | 15 kg/cm² G |
| --- | --- | --- |
| Carbon steel | 0.7 mm/year | Unmeasurable due to heavy corrosion |
| SUS 316 | 0.21 mm/year | Unmeasurable due to heavy corrosion |
| Double phase stainless steel (DP-3) | 0.03 mm/year | 16.6 mm/year |
| NAR-25-50MTi | <0.01 mm/year | 19.5 mm/year |
| Hastelloy C-22 | <0.01 mm/year | 10.3 mm/year |

It is understood from Table 2 that the corrosion of the metals used for the construction of the reactor is suppressed under the pressure condition under which HF is not liquefied according to the present invention, while the metals are excessively corroded under the pressure condition under which HF is liquefied, when the reaction temperature is the same.

EXAMPLE 3

The fluorination was carried out in the same manner as in Example 1 except that the reaction temperature was changed. In this example, 80° C. was the temperature condition at which HF was liquefied in the reaction mixture under the reaction pressure of 6 kg/cm²G, while 120° C. was the temperature condition at which HF was not liquefied. The results are shown in Table 3.

TABLE 3

| Metal | 80° C. | 120° C. |
| --- | --- | --- |
| Carbon steel | Unmeasurable due to heavy corrosion | 0.84 mm/year |
| SUS 316 | Unmeasurable due to heavy corrosion | 0.33 mm/year |
| Double phase stainless steel (DP-3) | 16.2 mm/year | 0.1 mm/year |
| NAR-25-50MTi | 18.5 mm/year | <0.01 mm/year |
| Hastelloy C-22 | 9.7 mm/year | <0.01 mm/year |

It is understood from Table 3 that the corrosion of the metals used for the construction of the reactor is suppressed under the temperature condition at which HF is not liquefied according to the present invention, while the materials are excessively corroded under the temperature condition at which HF is liquefied, when the reaction pressure is the same.

EXAMPLE 4

The fluorination was carried out in the same manner as in Example 1 except that the index y in $SbCl_xF_y (x+y=5)$ was changed. The results are shown in Table 4.

TABLE 4

| Metal | y = 1 | y = 4 |
| --- | --- | --- |
| Carbon steel | 0.69 mm/year | 0.78 mm/year |
| SUS 316 | 0.21 mm/year | 0.29 mm/year |
| Double phase stainless steel (DP-3) | 0.05 mm/year | 0.09 mm/year |
| NAR-25-50MTi | <0.01 mm/year | <0.01 mm/year |
| Hastelloy C-22 | <0.01 mm/year | <0.01 mm/year |

It is understood from the above results that the metals used for the construction of the reactors are not excessively corroded under the pressure and temperature conditions under which HF is not liquefied, if the index y of $SbCl_xF_y$ changes.

EXAMPLE 5

The reaction in this Example was performed using the same apparatus as used in Example 1 but an equipment for recycling unreacted materials (R31, R30 and HF) was attached to the apparatus.

The specific amount of the catalyst of $SbCl_xF_y$ (x+y=5) in which y had been adjusted to 2 was charged in the apparatus, and the molar ratio of supplied HF to supplied R30 was adjusted to about 2. The reaction pressure was 6 kg/cm²G.

The reaction temperature was kept at 90°0 C. which is 5° C. higher than the boiling point of HF under the pressure of 6 kg/cm²G, that is, 85°C., so that HF was not liquefied under the pressure of 6 kg/cm²G.

The concentration of $SbCl_xF_y$ in the reaction mixture was adjusted to 50 mole %.

The reaction mixture was recovered through the reflux condenser, and separated to obtain the reaction product (the mixture of R32 and HCl) and the unreacted materials (the mixture of R31, R30 and HF) as follows:

The recovered reaction mixture was introduced in a distillation column made of SUS 316 and distilled under 5 kg/cm²G.

The mixture consisting mainly of R32 as the reaction product and HCl was allowed to flow out from the condenser while maintaining the top temperature at about –26° C., and the mixture of unreacted R31, R30 and HF was discharged from the bottom of the distillation column. The mixture of the unreacted materials was recycled to the reactor.

When the reaction was stabilized, the organic materials and acids contained in the reaction mixture, the exit gas from the reflux condenser attached to the reactor, the exit gas from the recycling equipment and the recycled liquid were analyzed, and their compositions were determined. The results are shown in Table 5.

The composition of the antimony chlorofluoride used as the catalyst was analyzed, and the index y was 2.2.

TABLE 5

| Component | Reaction mixture (mole %) | Exit gas from the condenser (mole %) | Exit gas from the recycling equipment (mole %) | Recycled Liquid (mole %) |
| --- | --- | --- | --- | --- |
| HCl | | 33.5 | 67.0 | |
| HF | | 27.7 | 0.6 | 54.9 |
| R32 | 0.4 | 16.7 | 32.2 | 1.2 |
| R31 | 4.8 | 10.0 | 0.2 | 19.9 |
| R30 | 46.2 | 12.0 | | 24.0 |
| R40's | | 67 ppm | 131 ppm | |
| $SbCl_xF_y$ | 48.6 | | | |

The above results indicate that the concentration of the catalyst in the liquid reaction mixture and the index y of the catalyst were controlled stably, that the conversions of R30 and HF in the exit gas from the recycling equipment were very high and both higher than 99 mole %, and that the amounts of the by-products other than R30 were very low, that is, less than 0.1% per produced R32.

EFFECTS OF THE INVENTION

The reactor made of the metal such as Hastelloy C-22 or NAR-25-50MTi is not corroded by the reaction using the antimony chlorofluoride and HF which are highly corrosive, when the reaction is carried out under the conditions according to the present invention. The conversions of R30 and HF can be increased greatly, and the amounts of the by-products other than R30 are very low, typically less than 0.1% per produced R32, when the unreacted materials are recycled.

What is claimed is:

1. A process for preparing difluoromethane comprising reacting dichloromethane and hydrogen fluoride in a liquid phase in the presence of a fluorination catalyst, wherein the reaction pressure is between 1 and 10 kg/cm²ab., and the reaction temperature is between 50° and 150° C., provided that the selected reaction temperature is a temperature at which hydrogen fluoride is not liquefied under the selected reaction pressure.

2. The process according to claim 1, wherein the fluorination catalyst is an antimony chlorofluoride of the general formula:

$$SbCl_xF_y$$

wherein x+y=5.

3. The process according to claim 2, wherein y is a number of between 1 and 4.

4. The process according to claim 2, wherein y is a number of between 0.5 and 1.

5. The process according to claim 1, wherein the content of the catalyst in the liquid reaction mixture is between 10 and 90 mole %.

6. The process according to claim 1, wherein the reaction temperature is at least 5° C. higher than the boiling point of hydrogen fluoride under the selected reaction pressure.

7. The process according to any claim 1, which comprises the steps of:

(1) charging the fluorination catalyst into a reactor, (2) charging dichloromethane and hydrogen fluoride into the reactor and reacting them, (3) recovering a portion or whole of the reaction mixture from the reactor, (4) separating the recovered reaction mixture to obtain a mixture containing mainly difluoromethane as the reaction product and hydrogen chloride and another mixture containing unreacted dichloromethane, hydrogen fluoride and intermediate chlorofluoromethane, (5) isolating difluoromethane from the mixture containing difluoromethane and hydrogen chloride, and (6) recycling the mixture containing dichloromethane, hydrogen fluoride and chlorofluoromethane.

8. The process according to claim 7, which is performed continuously.

9. The process according to claim 1, wherein the reactor has a reflux column and a reflux condenser.

* * * * *